United States Patent

Wiesel

[11] Patent Number: 6,106,293
[45] Date of Patent: Aug. 22, 2000

[54] METHODS FOR WHITENING TEETH

[76] Inventor: Peter E. Wiesel, 222 New Rd., Central Park East, Suite 401, Linwood, N.J. 08221

[21] Appl. No.: 09/205,220

[22] Filed: Dec. 4, 1998

[51] Int. Cl.[7] ........................................................ A61C 5/00
[52] U.S. Cl. .............................................................. 433/215
[58] Field of Search .............................. 433/215, 217.1, 433/216; 424/53

[56] References Cited

U.S. PATENT DOCUMENTS

| | | | |
|---|---|---|---|
| 4,990,089 | 2/1991 | Munro | 433/215 |
| 5,032,178 | 7/1991 | Cornell | 433/216 |
| 5,098,303 | 3/1992 | Fischer | 433/215 |
| 5,240,415 | 8/1993 | Haynie | 433/217.1 |
| 5,575,654 | 11/1996 | Fontenot | 433/215 |
| 5,616,140 | 4/1997 | Prescott | 606/10 |
| 5,645,428 | 7/1997 | Yarborough | 433/215 |
| 5,713,738 | 2/1998 | Yarborough | 433/215 |
| 5,766,011 | 6/1998 | Sibner | 433/215 |
| 5,785,527 | 7/1998 | Jensen et al. | 433/215 |
| 5,891,453 | 4/1999 | Sagel et al. | 424/401 |

Primary Examiner—Nicholas D. Lucchesi
Attorney, Agent, or Firm—Norman E. Lehrer

[57] ABSTRACT

Methods for whitening a person's teeth are disclosed. In a first embodiment, the steps include providing a carrier, such as a transparent tape, where the carrier contains a catalyst thereon, and preparing a mixture which includes an oxygen radical generating agent and a buffer. The mixture is then applied to the carrier and the carrier is applied to a person's teeth. The person's teeth are then exposed to a light source. In another embodiment of the present invention, the mixture may include an oxygen radical generating agent, a catalyst, and a buffer. The mixture is then applied to a carrier which is applied to the person's teeth. The person's teeth are then exposed to a light source. In yet another embodiment, a mixture of an oxygen radical generating agent, a thickening agent, and a buffer is prepared and applied to a carrier. The carrier is then applied to a person's teeth which are then exposed to a light source. This carrier may be covered with a layer of release paper prior to use and packaged in a sterile container. In another embodiment a carrier, similar in structure to the carriers described above, is provided. A mixture of bleaching agents, without a catalyst, is then applied to the carrier by the dentist. The tape is then applied to the patient's teeth which are then exposed to a laser light.

28 Claims, No Drawings

METHODS FOR WHITENING TEETH

BACKGROUND OF THE INVENTION

The present invention is directed toward methods for whitening a person's teeth and more particularly, toward a method where a carrier has bleaching agents applied thereto and the carrier is applied to a person's teeth whereupon the teeth are exposed to a light source in order to enhance the effectiveness of the bleaching agents.

Currently, dentists whiten a patient's teeth by preparing a peroxide solution and coating the teeth with the solution. Once the solution is placed on the teeth, the teeth are exposed to a heat lamp or a laser light in order to heat the peroxide and to accelerate the bleaching process. In order to protect the patient's gums, a rubber sheet, Vaseline, or a light cured gel may be placed on the gums.

There are several disadvantages with the above-described process. For example, the rubber sheet placed over the patient's gums may stretch so that the peroxide solution leaks around the rubber sheet, exposing the patient's gums to the peroxide, thereby causing the patient discomfort. Also, this method cannot be performed on the upper set of teeth and the lower set of teeth simultaneously. Rather, only one set of teeth may be whitened at a time. Another disadvantage is that if a heat lamp is used a substantial amount of time is required in order to effectively bleach the teeth. Thus, the patient is exposed to the lamp for a great deal of time. This can cause extreme discomfort and inconvenience to the patient. Furthermore, the peroxide solution often times cannot be concentrated on the teeth. That is, the solution may drip off of the teeth if too much of the solution is applied or the solution may dry out if too little of the solution is applied.

Another method of whitening teeth is disclosed in U.S. Pat. No. 5,645,428 to Yarborough. This patent discloses using a laser light to activate bleaching agents applied to a patient's teeth. A mixture of peroxide and a first catalyst is prepared and then applied to the teeth. The teeth are then exposed to a laser light which activates the peroxide and catalyst to accelerate the bleaching process without heat. A second mixture of peroxide and a catalyst is then prepared and applied to the teeth. Again, the teeth are exposed to a laser light which heat activates the second mixture to accelerate the bleaching process. This process, however, increases the patient's exposure to laser light.

In yet another system, a peroxide solution may be combined with a gel which acts as a carrier. The mixture is then applied to a person's teeth which are then exposed to a light source. This system may be used by a person without the aid of a dentist or other medical personnel. That is, the peroxide-gel solution may be placed within a plastic mouthguard which is worn by a person overnight. A problem with this system is that the peroxide-gel solution decreases the effectiveness of the peroxide because generally these solutions are weak.

Also, the use of gel, in any dental office system, decreases the effectiveness of the peroxide because of the gel's opacity. That is, light is not able to pass through to all of the peroxide because of the opacity of the gel. Also, the gel prevents full contact of the tooth with the peroxide solution, thereby decreasing the effectiveness of the peroxide solution.

SUMMARY OF THE INVENTION

The present invention is designed to overcome the deficiencies of the prior art discussed above. It is an object of the present invention to provide a method for whitening a person's teeth which decreases the amount of time the person is exposed to a laser light.

It is a further object of the present invention to provide a method of whitening teeth which is more efficient and less time-consuming than the methods currently being used.

In accordance with the illustrative embodiments demonstrating features and advantages of the present invention, there is provided a method for whitening a person's teeth which includes the steps of providing a carrier, such as a transparent tape, which contains a catalyst thereon, and preparing a mixture which includes an oxygen radical generating agent and a buffer. The mixture is then applied to the carrier and the carrier is applied to a person's teeth. The person's teeth are then exposed to a light source. In another embodiment of the present invention, the mixture may include an oxygen radical generating agent, a catalyst, and a buffer. The mixture is then applied to a carrier which is applied to the person's teeth. The person's teeth are then exposed to a light source.

In yet another embodiment, a mixture of an oxygen radical generating agent, a thickening agent, and a buffer is prepared and applied to a carrier. The carrier is then applied to a person's teeth which are then exposed to a light source. This carrier may be covered with a layer of release paper prior to use and packaged in a sterile container. This embodiment may be used by a person in his or her home without the aid of a dentist or any other medical personnel. In another embodiment, a carrier, similar in structure to the carriers described above, is provided. A mixture of bleaching agents, without a catalyst, is then applied to the carrier by the dentist. The tape is then applied to the patient's teeth which are then exposed to a laser light.

Other objects, features, and advantages of the present invention will be readily apparent from the following detailed description of preferred embodiments thereof.

DETAILED DESCRIPTION OF THE PREFERRED EMBODIMENTS

A first embodiment of the teeth whitening method of the present invention essentially includes the steps of providing a carrier which may be, for example, a transparent tape or the like. The tape may have straight or scalloped edges in order to follow the contour of the gum line once the tape is adhered to a person' teeth as will be discussed in more detail below. The tape may be made from a biocompatible material and can be made in a variety of sizes and shapes to allow for the tape to fit over the teeth of a child, a teenager, or an adult.

A heat enhancer, catalyst, or any substance that causes a change in the rate of a chemical reaction without itself being consumed by the reaction is then applied to the carrier. The heat enhancer may be Beta carrotene, ferrous oxide, or other similar types of catalysts. The catalyst may be coated onto or impregnated into the surface of the carrier. A mixture of bleaching agents is then applied to the tape by the dentist. The bleaching agents may be a mixture of an oxygen radical generating agent such as a peroxide and a buffer. The preferred peroxide is hydrogen peroxide although any peroxide selected from the group consisting of hydrogen peroxide, carbamide peroxide, calcium bicarbonate peroxide, sodium bicarbonate peroxide, and any other oxygen radical generating agent may be used. The preferred buffer is sodium hydroxide although any buffer selected from the group consisting of sodium hydroxide, sodium carbonate, sodium bicarbonate, calcium carbonate, calcium bicarbonate, potassium hydroxide, calcium hydroxide, and any other buffering agent may be used. A preferred ratio of hydrogen peroxide to sodium hydroxide is 35:5; however, this ratio may be varied as needed. Also, the concentration of the peroxide may vary, for example, a concentration between 30–50% may be used.

Once the patient's teeth are cleaned and prepared for the treatment, the tape, with the mixture thereon, is applied or unfolded onto the teeth with the scalloped edges of the tape fitting along the person's gum line. The mixture remains on the carrier and the carrier remains on the person's teeth due to surface tension. The heat enhancer reacts with the mixture of bleaching agents, creating heat and accelerating the otherwise slow bleaching effects of the peroxide. The person's teeth are then exposed to virtually any light source in order to further accelerate heating of the peroxide, thereby accelerating the bleaching of the teeth. The light source, for example, may be a heat lamp, a carbon dioxide laser, any short or long wave infrared laser, an argon laser, an utraviolet laser, or a Yttrium Arsenic Gallium (YAG) laser.

The second embodiment of the present invention is similar to the first embodiment; however, the carrier is not coated with a heat enhancer, rather, the enhancer is mixed with the oxygen radical generating agent and buffer. This mixture is then applied to the carrier surface and the carrier is applied to the person's teeth as in the first embodiment. Again, as in the first embodiment, the person's teeth are exposed to a light source which may be any of the sources discussed above. Also as in the first embodiment, the oxygen radical generating agent, buffer, and heat enhancer may be selected from their respective groups listed above. Furthermore, the carrier has scalloped edges and may be made from the same material and in the same sizes as described above.

In a third embodiment of the present invention, the carrier is coated with a thickened layer of the mixture containing an oxygen radical generating agent and a buffer. Also included in this mixture is a thickening agent such as silica dioxide. However, the thickening agent may be selected from the group consisting of silica dioxide, silicates, cellulose compounds such as hydroxyethylcellulose, lanolate, palmitate, oleate, sodium stearate, and other fatty acids. Alternatively, a substance containing sodium monoflurophosphate may be embedded into the carrier. In this embodiment, unlike the previous embodiments, release paper may be applied to the thickened layer, thereby covering the layer. The carrier may be stored in a sterile package in a rolled form or in differently sized strips. As in the previous embodiments, the oxygen radical generating agent and buffer may be selected from their respective groups as discussed above. Also, the carrier may have scalloped edges and may be made from the same material and in the same sizes as described above. Furthermore, the back of the carrier may have designs thereon which appeal to children.

In order to use the device described in the third embodiment, a person removes the rolled carrier or tape from the package and unrolls as much of the tape as desired and releases the desired portion from the rest of the roll. Alternatively, if the tape is packaged in strips, the person simply removes the desired strip from the package. The person then removes the release paper from the tape and places or folds the tape against his or her teeth with the scalloped edges aligned with the gum line. The person may wear the tape throughout the day with the teeth being exposed to natural light. Thus, the person's teeth are whitened. Accordingly, a person may use the device without the aid of a dentist or other medical personnel.

In another embodiment of the present invention, a carrier, having a structure as described above, is provided. A dentist may then prepare a mixture of bleaching agents, containing, for example, an oxygen radical generating agent and a buffer selected from the groups discussed. The dentist may then coat the carrier with the mixture. This embodiment, however, does not include a heat enhancer. Alternatively, the mixture may include just a peroxide solution, when the amount of bleaching is very light. The carrier is then placed on a person's teeth in the manner described above and the patient's are teeth exposed to a laser light source.

With all of the embodiments described above, with the exception of the home use carrier, additional mixture may be added to the carrier if desired. That is the dentist may brush or otherwise apply more of the mixture onto the tape. Also, the carrier or tape may be stored in a dispenser, with the dentist dispensing the amount of tape that he needs for a particular patient.

An advantage of the present system is that because the mixtures are placed on the carriers, the mixture remains concentrated and remains on the person's teeth, thereby increasing the efficiency of the whitening process. Also, the use of a heat enhancer eliminates the need for a laser light source. That is, because the heat enhancer acts as a catalyst, thereby accelerating the reaction of the peroxide mixture, any light source may be used and laser light need not be used. As a result, the possibility of side effects a person may experience due to the use of a laser light is decreased. Furthermore, the use of a transparent tape or carrier also increases the efficiency of the whitening process in that the light source, whatever it may be, is not blocked, rather, the transparent nature of the carrier facilitates the exposure of the teeth to the light source.

The present invention may be embodied in other specific forms without departing from the spirit or essential attributes thereof and accordingly, reference should be made to the appended claims rather than to the foregoing specification as indicating the scope of the invention.

I claim:

1. A method for whitening a person's teeth comprising the steps of:

providing a carrier containing means for enhancing heat;

preparing a mixture of bleaching agents;

applying said mixture to said carrier so that said mixture reacts with said means for enhancing heat;

applying said carrier to the person's teeth; and exposing the person's teeth to a light source.

2. The method for whitening a person's teeth of claim 1 wherein said carrier is a transparent tape with scalloped edges.

3. The method for whitening a person's teeth of claim 1 wherein said heat enhancing means is a catalyst.

4. The method for whitening a person's teeth of claim 3 wherein said catalyst is ferrous oxide.

5. The method for whitening a person's teeth of claim 1 wherein said bleaching agents comprise an oxygen radical generating agent and a buffer.

6. The method for whitening a person's teeth of claim 5 wherein said oxygen radical generating agent is a peroxide and said buffer is sodium hydroxide.

7. The method for whitening a person's teeth of claim 1 wherein said light source is laser light.

8. A method for whitening a person's teeth comprising the steps of:

providing a carrier;

preparing a mixture comprising means for enhancing heat and bleaching agents;

applying said mixture to said carrier;

applying said carrier to the person's teeth; and exposing the person's teeth to a light source.

9. The method for whitening a person's teeth of claim 8 wherein said carrier is a transparent tape with scalloped edges.

10. The method for whitening a person's teeth of claim 8 wherein said heat enhancing means is a catalyst.

11. The method for whitening a person's teeth of claim 10 wherein said catalyst is ferrous oxide.

12. The method for whitening a person's teeth of claim 8 wherein said bleaching agents comprise an oxygen radical generating agent and a buffer.

13. The method for whitening a person's teeth of claim 12 wherein said oxygen radical generating agent is a peroxide and said buffer is sodium hydroxide.

14. The method for whitening a person's teeth of claim 8 wherein said light source is laser light.

15. A method for whitening a person's teeth comprising the steps of:

providing a carrier;

preparing a mixture of bleaching agents and a thickening agent;

applying said mixture to said carrier;

applying said carrier to the person's teeth; and exposing the person's teeth to a light source.

16. The method for whitening a person's teeth of claim 15 wherein said carrier is a transparent tape with scalloped edges.

17. The method for whitening a person's teeth of claim 16 further including the step of providing a release paper covering said tape prior to use.

18. The method for whitening a person's teeth of claim 15 wherein said bleaching agents comprise an oxygen radical generating agent and a buffer.

19. The method for whitening a person's teeth of claim 18 wherein said oxygen radical generating agent is a peroxide and said buffer is sodium hydroxide.

20. The method for whitening a person's teeth of claim 15 wherein said light source is natural light.

21. A method for whitening a person's teeth comprising the steps of:

providing a transparent tape;

preparing a mixture of bleaching agents;

applying said mixture to said tape;

applying said tape to the person's teeth; and exposing the person's teeth to a laser light.

22. The method for whitening a person's teeth of claim 21 including the step of exposing the person's teeth to a laser light source.

23. The method for whitening a person's teeth of claim 21 including the step of exposing the person's teeth to a source of visible light.

24. A method for whitening a person's teeth comprising the steps of:

providing a carrier;

providing a bleaching agent;

applying said bleaching agent to said carrier;

applying said carrier to the person's teeth; and exposing the person's teeth to a source of light.

25. The method for whitening a person's teeth of claim 24 wherein said carrier is a transparent tape.

26. The method for whitening a person's teeth of claim 25 further including the step of providing a release paper covering said tape prior to use.

27. The method for whitening a person's teeth of claim 24 wherein said bleaching agent comprises an oxygen radical generating agent.

28. The method for whitening a person's teeth of claim 27 wherein said oxygen radical generating agent is a peroxide.

\* \* \* \* \*

UNITED STATES PATENT AND TRADEMARK OFFICE
CERTIFICATE OF CORRECTION

PATENT NO. : 6,106,293
DATED : August 22, 2000
INVENTOR(S) : Peter E. Wiesel

It is certified that error appears in the above-identified patent and that said Letters Patent is hereby corrected as shown below:

Column 6,
Line 12, "a laser" should be deleted.

Signed and Sealed this

Twentieth Day of November, 2001

Attest:

NICHOLAS P. GODICI
Attesting Officer
Acting Director of the United States Patent and Trademark Office